(12) United States Patent
Ota et al.

(10) Patent No.: US 7,621,110 B2
(45) Date of Patent: Nov. 24, 2009

(54) SELF-HEATING AND ADHESIVE DEVICE

(75) Inventors: Keizo Ota, Takefu (JP); Tetsuhiro Watanabe, Takefu (JP)

(73) Assignee: Ohshin MLP Co., Ltd., Echizen-shi, Fukui (JP)

( * ) Notice: Subject to any disclaimer, the term of this patent is extended or adjusted under 35 U.S.C. 154(b) by 785 days.

(21) Appl. No.: 11/405,147

(22) Filed: Apr. 17, 2006

(65) Prior Publication Data

US 2006/0210752 A1     Sep. 21, 2006

Related U.S. Application Data

(62) Division of application No. 10/793,673, filed on Mar. 4, 2004, now abandoned.

(51) Int. Cl.
*B65B 51/10*     (2006.01)
(52) U.S. Cl. .................. 53/477; 126/263.02; 156/145; 156/250
(58) Field of Classification Search ............ 126/263.02, 126/263.07, 263.05; 53/477; 156/145, 326, 156/250
See application file for complete search history.

(56) References Cited

U.S. PATENT DOCUMENTS

2004/0178384 A1*  9/2004  Usui ........................... 252/76

* cited by examiner

*Primary Examiner*—Michael C Miggins
(74) *Attorney, Agent, or Firm*—Osha • Liang LLP

(57) ABSTRACT

The self-heating and adhesive device of the present invention comprises a gas-permeable sheet layer, an exothermic composition layer, a gas-impermeable sheet layer, a support, a poultice or gel layer, and a releasing sheet layer in this order, wherein the exothermic composition layer is stuffed in a pouch that is made of the gas-permeable sheet layer and the gas-impermeable sheet layer, and wherein the support comprises a fibrous layer only or a gas-impermeable sheet and a fibrous layer and has a moisture permeability within the range of 0 to 3,000 g/m²·24 hours by the Lyssy method.

8 Claims, 1 Drawing Sheet

SELF-HEATING AND ADHESIVE DEVICE

CROSS-REFERENCE TO RELATED APPLICATIONS

This is a Divisional Application of U.S. patent application Ser. No. 10/793,673, filed on Mar. 4, 2004, now abandoned.

FIELD OF INVENTION

This invention relates to a self-heating and adhesive device comprising a layer of an exothermic composition and a layer of an adhesive poultice or gel.

Further, this invention relates to an adhesive structure comprising a layer of an adhesive poultice or gel. This structure is useful to produce the self-heating and adhesive device.

BACKGROUND

Self-heating and adhesive devices have been produced, for example, as follows:
1) bonding or heat-sealing a gas-permeable sheet and a gas-impermeable sheet to make a pouch having an opening;
2) stuffing an exothermic composition into the pouch;
3) closing the opening of the pouch by bonding or heat-sealing;
4) preparing a composite of a support and an adhesive poultice or gel whose surface is covered with a releasing sheet;
5) bonding an outer surface of the support to an outer surface of the gas-impermeable sheet by using an adhesive that has been applied to the gas-impermeable sheet; and
6) cutting off one self-heating and adhesive device.

The poultice or gel layer is commonly produced by applying an aqueous composition onto one surface of the support and then making water-soluble polymers contained in the composition closslink with crosslinking agents. However, when unwoven fabric is used as the support, the aqueous composition sometimes permeates through the unwoven fabric to get to the other side of it during the application, or after the application and before the completion of the closslinking. This is disclosed in Japanese Patent Early-publication No. 2000-119128. If the aqueous composition gets to the other side of the unwoven fabric, the adhesive force between the gas-impermeable sheet and the support, i.e., the unwoven fabric, lowers, which causes insufficient adhesion or the worst case where the gas-impermeable sheet and the support do not adhere to each other.

Self-heating and adhesive devices in which the adhesion between gas-impermeable sheet and the support is insufficient cannot be sold. Thus, if the aqueous composition permeates through the support to get to the other side of it, a yield factor lowers.

Japanese Patent Early-publication Nos. Hei. 08-336554, Hei. 10-152432, and Hei. 05-170644, each of which discloses an invention of a self-heating and adhesive device, show that there may be a support between an adhesive layer such as a poultice layer and a film or sheet that constitutes a part of an exothermic portion of the self-heating and adhesive device. However, they do not mention the permeation of the aqueous composition through the support and the lowering of the adhesive force that is caused by the permeation. Japanese Patent Early-publication No. Hei. 05-170644 shows that the support is adhered to the film or sheet that constitutes a part of an exothermic portion and then the adhesive layer such as the poultice layer is made on the support. Thus, by the method that is disclosed in Japanese Patent Early-publication No. Hei. 05-170644, the problem of the lowering of the adhesive force between the film or sheet and the support is not caused.

As a means for preventing the permeation of the aqueous composition through the support such as an unwoven fabric, it is proposed that an aqueous composition that will turn to the adhesive poultice or gel layer and that comprises a closslinking agent in a larger amount is used to closslink water-soluble polymers faster. By this means, the permeation of the aqueous composition may be surely prevented. However, if the closslinking agent is used in a large amount, the closslinking of the water-soluble polymers takes place over a long period of time and finally the poultice or gel layer becomes to non-adhesive. This means that the self-heating and adhesive device is insufficient in view of the storage stability.

An object of this invention is to prevent, by a means in which an amount of a closslinking agent is not increased, permeation of an aqueous composition through a support while an adhesive poultice or gel layer is made and aged.

Another object of this invention is to maintain the adhesiveness of the poultice or gel layer for a longer period of time.

SUMMARY

The present inventors had extremely studied to attain the above objects. As a result, they have accomplished the present invention.

Namely, the present invention relates to a self-heating and adhesive device comprising a gas-permeable sheet layer, an exothermic composition layer, a gas-impermeable sheet layer, a support, a poultice or gel layer, and a releasing sheet layer in this order, wherein the exothermic composition layer is stuffed in a pouch that is made of the gas-permeable sheet layer and the gas-impermeable sheet layer, and wherein the support comprises a fibrous layer only or a gas-impermeable sheet and a fibrous layer and has a moisture permeability within the range of 0 to 3,000 g/m$^2$·24 hours by the Lyssy method (JIS K 7129, ASTM E 398).

This device may further comprise at least one adhesive layer which bonds any two components of the device.

Also, the present invention relates to an adhesive structure comprising a support, an adhesive poultice or gel layer, and a releasing sheet layer in this order, wherein the support comprises a fibrous layer only or a gas-impermeable sheet and a fibrous layer and has a moisture permeability within the range of 0 to 3,000 g/m$^2$·24 hours by the Lyssy method (JIS K 7129, ASTM E 398).

This structure may further comprise at least one adhesive layer that bonds any two components of the device.

DETAILED DESCRIPTION

Hereafter, the present invention is particularly explained.

Figure 1:
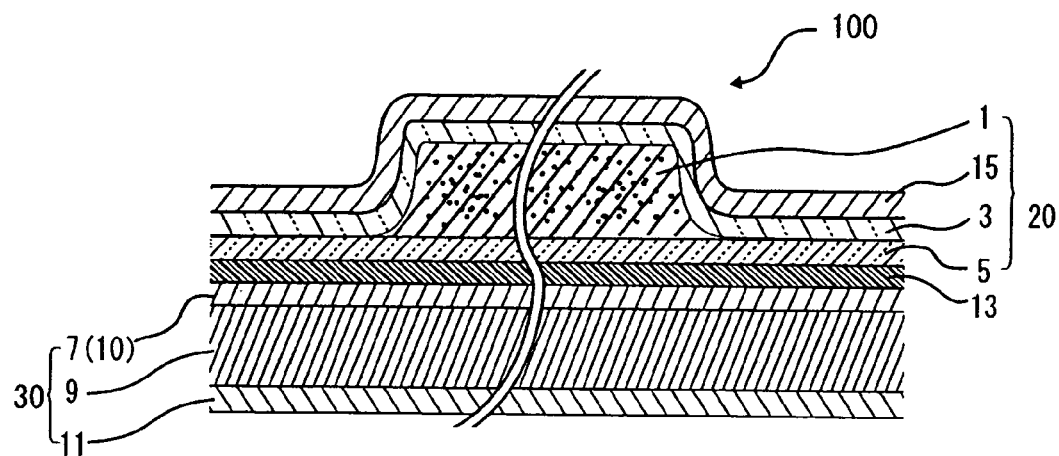
FIG. 1 is a sectional view of a first embodiment of the device according to the present invention.
Figure 2:
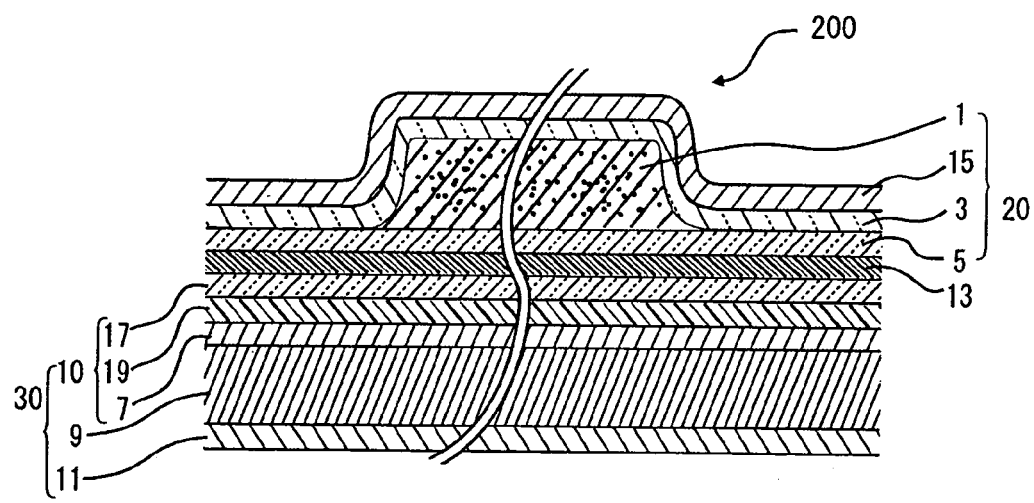
FIG. 2 is a sectional view of a second embodiment of the device according to the present invention.

First, with referring to FIGS. 1 and 2, the constitution of the device of the present invention is explained.

FIG. 1 is a sectional view of a first embodiment of the device according to the present invention. The device 100 comprises a gas-permeable sheet layer 3 on one surface of an exothermic composition layer 1 and an unwoven fabric layer 15 on the outer surface of the gas-permeable sheet layer 3, and on another surface of the exothermic composition layer 1 a gas-impermeable sheet layer 5, an adhesive layer 13, an unwoven fabric layer 7 as a fibrous layer, a poultice or gel layer 9, and a releasing sheet layer 11 in this order. The unwoven fabric layer 15, the gas-permeable sheet layer 3, the exothermic composition layer 1, and the gas-impermeable sheet layer 5 constitute an exothermic portion 20. The gas-permeable sheet layer 3 and the gas-impermeable sheet layer 5 constitute a pouch. In this pouch an exothermic composition is stuffed, which generates heat in the presence of oxygen. In this embodiment, a support 10 is constituted of only the unwoven fabric layer 7 as the fibrous layer.

FIG. 2 is a sectional view of the second embodiment of the device according to the present invention. This device 200 comprises a gas-permeable sheet layer 3 on one surface of an exothermic composition layer 1 and an unwoven fabric layer 15 on the outer surface of the gas-permeable sheet layer 3, and on another surface of the exothermic composition layer 1 a gas-impermeable sheet layer 5, an adhesive layer 13, a gas-impermeable sheet 17, an adhesive layer 19, an unwoven fabric layer 7 as a fibrous layer, a poultice or gel layer 9, and a releasing sheet layer 11 in this order. The unwoven fabric layer 15, the gas-permeable sheet layer 3, the exothermic composition layer 1, and the gas-impermeable sheet layer 5 constitute an exothermic portion 20. The gas-permeable sheet layer 3 and the gas-impermeable sheet layer 5 constitute a pouch. In this pouch an exothermic composition is stuffed, which generates heat in the presence of oxygen. In this embodiment, the unwoven fabric layer 7 as a fibrous layer is applied on the gas-impermeable sheet 17 with the adhesive layer 19 to be a composite that is a support 10. The unwoven fabric layer 7 may bond to the gas-impermeable sheet 17 without the adhesive layer 19 by, e.g., a melt-bonding such as a heat-sealing.

In the devices 100 and 200, the outermost layer is the unwoven fabric layer 15. This unwoven fabric layer 15 is not an essential component of the device according to the present invention. However, this layer 15 contributes to an improvement of touch and a maintenance of the form of a device.

Also, the adhesive layers 13 and 19 are not essential components of the device according to the present invention. When an adhesive or tacky composition is used to bond one essential component to another essential component, an adhesive layer is made. The adhesive or tacky composition that is used in the present invention is known in this technical field. One example of it is a composition of which main component is a styrene-isoprene-styrene block copolymer.

The exothermic composition layer of the device according to the present invention is constituted of an exothermic composition that generates heat in the presence of oxygen. The components that are contained in the exothermic composition are not limited as long as they have been used in the conventional exothermic compositions. Examples of the components are as follows:

Examples of chemical exothermic agents include metal powders such as iron powder, especially reduced iron powder and atomized iron powder. Examples of reaction auxiliaries include metal halides such as sodium chloride, potassium chloride, magnesium chloride, calcium chloride, iron (II) chloride, and iron (III) chloride; and metal sulfates such as potassium sulfate, sodium sulfate, magnesium sulfate, copper (II) sulfate, iron (II) sulfate, and iron (III) sulfate. Examples of water retaining agents include active carbon, alumina, silica gel, zeolite, wood charcoal, and water-absorptive polymers. Of course, water is also used. Examples of other additives include polymers such as carboxymethyl cellulose, acrylic acid starch, polyethylene, polypropylene, and polystyrene; bentonite, vermiculite, and pearlite.

It is preferable that an exothermic composition having a formula is used such that a metal powder such as iron powder does not have a tendency of deflection.

In the present invention, the exothermic composition is processed to be a form of sheet. The thickness of the sheet may be 5 mm or less, 0.5 to 4 mm, or 1 to 2 mm.

The pouch that constitutes the exothermic portion of the device according to the present invention comprises a gas-permeable sheet in one side and a gas-impermeable sheet in another side.

An example of the gas-permeable sheet is a gas-impermeable polymer film having openings, e.g., a moisture-permeable porous film. In this specification and claims, the term "moisture permeability" may be used. If moisture can pass through, gas can also pass through. Namely, one having a moisture-permeability has a gas-permeability.

The device of the present invention may have a layer or layers on or out of the gas-permeable sheet layer. However, the layer or layers should have a gas-permeability. Examples of the layers include a woven fabric layer, an unwoven fabric layer, a knit layer, and a paper layer.

The gas-permeability of a gas-permeable side of a pouch affects the exothermic property of the exothermic composition that is stuffed in the pouch. Thus, it is preferable to select and process a material or materials that constitute the gas-permeable side so that the gas-permeable has a moisture-permeability of 200 to 500 g/m$^2$·24 hours, especially 250 to 400 g/m$^2$·24 hours by the Lyssy method (JIS K 7129).

The Lyssy method is compliant to industry standards of many countries. In, e.g., JIS Z 0208, JIS K 7129, and ASTM E 398, the measurement by the Lyssy method is conducted at 40° C. under a difference of relative humidities of 90%. More particularly, a sample to be measured is inserted to the interface of an underneath chamber that lies under a condition of relative humidity of 100% and an upper chamber comprising a high-sensitive humidity sensor. The relative humidity of the upper chamber is maintained at 10%. Thus, the difference of the relative humidities is 90% (i.e., 100-10). Then, the time (seconds) to be required for increasing the relative humidity of the upper chamber from about 9% to about 11% is measured. By using a standard sample, of which the moisture permeability is known, the time is measured in the same way under the same condition. Comparing the data of the sample to be measured with that of the standard sample, the moisture permeability of the sample to be measured is decided.

Methods for processing materials that constitute a gas-permeable side of a pouch so that the gas-permeable side has a desirable gas-permeability are known in this technical field. Examples of the methods include one in which two or more gas-permeable sheets are used, the sheets are bonded one another, and the area ratio of the total area of the bonded portions to the area of the sheet is controlled, and another one by which a porous film having a desirable gas-permeability is prepared If a moisture-permeable porous film is used as the gas-permeable sheet, its thickness may be, but not limited thereto, 150 μm or less, 20 to 100 μm, or 40 to 60 μm. If a gas-permeable layer that is set out the gas-permeable sheet layer is made of a woven fabric, an unwoven fabric, or paper, the basis weight of the gas-permeable layer may be, but not limited thereto, 300 g/m$^2$ or less, 40 to 150 g/m$^2$, or 60 to 100 g/m$^2$.

Examples of a gas-impermeable sheet that can constitute another side of the pouch, i.e., the gas-impermeable side, include gas-impermeable polymer films such as polyethylene film. The thickness of the gas-impermeable polymer film may be, but not limited thereto, 100 μm or less, 10 to 70 μm, 20 to 50 μm, or 25 to 40 μm.

Examples of polymeric materials for the gas-permeable sheet and the gas-impermeable sheet include a polyethylene, a polypropylene, a polyester, a polyamide, a poly(vinyl chloride), a poly(vinylidene chloride), a polyurethane, a polystyrene, an ethylene-vinyl acetate copolymer, and a polycarbonate.

The gas-permeable sheet and the gas-impermeable sheet are not limited to monolayer films, but may be multilayer films.

At least one of the gas-permeable sheet and the gas-impermeable sheet may have a heat-seal property. If the gas-permeable sheet or the gas-impermeable sheet is made of a multilayer film, a layer that faces other sheet may have a heat-seal property. An example of a polymer film that shows the heat-seal property is a metallocene polyethylene film, which can be used in the present invention. The peripheries of the gas-permeable sheet and the gas-impermeable sheet that constitute the pouch may also be bonded each other with an adhesive or tacky composition.

The device of the present invention has, out the gas-impermeable sheet layer that constitute the pouch, i.e., in a side that faces to a human body, a poultice or gel layer and a support that supports the poultice or gel layer. One sided of the support faces to the gas-impermeable sheet layer that constitutes the pouch. The poultice or gel layer functions as an adhesive or tacky layer when the device is applied onto a human body. Therefore, before use, the poultice or gel layer is covered with a releasing sheet.

As shown in FIG. 1, in the first embodiment of the device according to the present invention the support 10 comprises the fibrous layer 7 only. As shown in FIG. 2, in the second embodiment of the device according to the present invention the support 10 comprises the gas-impermeable sheet 17 and the fibrous layer 7. In the latter case, one side of the gas-impermeable sheet 17 faces the gas-impermeable sheet layer 5 that constitutes the pouch.

The feature of the present invention is that the support has a moisture-permeability within the range of 0 to 3,000 $g/m^2 \cdot 24$ hours by the Lyssy method (JIS K 7129). The poultice or gel layer contains water. Therefore, if the support has a high moisture-permeability, the bonding between the support and the gas-impermeable sheet layer may become insufficient. However, if the support has a moisture-permeability within the above range, the water that is contained in the poultice or gel layer does not get to or slightly get to, by passing through the support, the adhesive layer lain between the support and the gas-impermeable sheet layer. Thus, the support can be bonded to the gas-impermeable sheet layer with a sufficient adhesive force.

If the support comprises a fibrous layer only, its moisture-permeability is 3,000 $g/m^2 \cdot 24$ hours or less, and may be 2,000 $g/m^2 \cdot 24$ hours or less, or 1,500 to 1,900 $g/m^2 \cdot 24$ hours.

If the support comprises a fibrous layer only, its moisture-permeability depends on the kind of the raw materials, the conditions after processing, the thickness, and the like. The fibrous layer may be made of at least one member selected from the group consisting of an unwoven fabric, a woven fabric, and paper. The fibrous layer may be made of an unwoven fabric, e.g., a melt-blow unwoven fabric. The unwoven fabric may have a basis weight in the range of 20 to 60 $g/m^2$, 30 to 50 $g/m^2$, or 35 to 45 $g/m^2$. When the basis weight is large, the moisture-permeability may be low. However, a too thick unwoven fabric tends to give a uncomfortable touch.

The raw materials for the fibrous layer may comprise, at least a part of it, at least one member selected from the group consisting of a polyester, a polypropylene, a polyamide (e.g., a nylon), and an acrylic. The raw materials may consist of at least one member selected from the group consisting of a polyester, a polypropylene, a polyamide (e.g., a nylon), and an acrylic.

If the support comprises a gas-impermeable sheet and a fibrous layer, the moisture-permeability of the support is near 0 $g/m^2 \cdot 24$ hours because of the presence of the gas-impermeable sheet. Therefore, in this case the raw materials, thickness, and the like of the fibrous layer can be selected from view points of, e.g., a touch, heat-conductivity, and an easiness in the production of the poultice or gel layer (an easiness in the coating or application of, e.g., a poultice composition).

Examples of the gas-impermeable sheet that constitutes the support include gas-impermeable polymer films, e.g., a polyethylene film. The thickness of the gas-impermeable sheet may be 60 μm or less, 10 to 40 μm, or 20 to 30 μm.

The fibrous layer that is used for the support with the gas-impermeable sheet may be made of at least one member selected from the group consisting of an unwoven fabric, a woven fabric, and paper. The fibrous layer may be made of an unwoven fabric, e.g., a spun-lace or melt-blow unwoven fabric. The unwoven fabric may have a basis weight in the range of 10 to 40 $g/m^2$, 15 to 35 $g/m^2$, or 20 to 30 $g/m^2$ In the case where the fibrous layer is used for the support with the gas-impermeable sheet, the raw materials for the fibrous layer may comprise, at least a part of it, at least one member selected from the group consisting of cotton, a regenerated cellulose (e.g., rayon), a polyester, a polypropylene, a polyamide (e.g., a nylon), and an acrylic. The raw materials may comprise, at least a part of it, at least one member selected from the group consisting of a polyester, a polypropylene, a polyamide (e.g., a nylon), and an acrylic. The raw materials may consist of at least one member selected from the group consisting of a polyester, a polypropylene, a polyamide (e.g., a nylon), and an acrylic.

The support that is a composite of the gas-impermeable sheet and the fibrous layer may be prepared by melt-bonding the gas-impermeable sheet and the fibrous layer or bonding them with a adhesive or tacky composition. In the latter case, an adhesive layer is prepared between them.

There is a poultice or gel layer on the fibrous layer that is just the support or that constitutes the support. The composition that is used to prepare the poultice or gel layer comprises a polymer or polymers such as a poly(vinyl pyrrolidone), a poly(vinyl alcohol), a poly(acrylic acid), a polyacrylate, an acrylic acid starch, a hydroxyethyl cellulose, and a carboxy methylcellulose; an excipient, filler, or vehicle such as kaolin and titanium oxide; a closslinking agent such as a polyvalent metal salt, a polyvalent metal hydroxide, and a polyvalent metal oxide; a polyhydric alcohol such as glycerol, sorbitol, and propylene glycol; a surfactant; a preservative or stabilizer; and other components that have been conventionally used in this technical field. The composition may comprise a polymer having a carboxyl group such as poly(acrylic acid) and as a closslinking agent for the polymer a polyvalent metal salt (e.g., aluminium hydroxide and magnesium metasilicate aluminate).

Examples of the compositions that constitute the poultice or gel layer include poultice compositions. The poultice compositions are commonly hydrophilic and contain water in an amount of about 50 to 60% by weight. The composition that constitutes the poultice or gel layer may also be a medicament-releasable composition. The composition of this type comprises any medicament such as indomethacin, a resolvent for the medicament such as castor oil and alcohols, and an excipient, filler, or vehicle such as various polymers and clay minerals. The medicament-releasable composition may be hydrophilic or lipophilic. Further, the composition that constitutes the poultice or gel layer may be a hydrogel composition comprising, e.g., a polysaccharide as its main component, which also comprises or does not comprise a medicament.

In the present invention, the thickness of the poultice or gel layer is not particularly limited. From the view points of heat conductive property and touch, it may be 2 mm or less, 0.2 to 1.5 mm, or 0.5 to 1 mm.

The device of the present invention is applied to a human body only by the adhesive force of the poultice or gel layer. Therefore, the layer should have an adhesive force that enables the device to be held on the human body. However, if the adhesive force is too strong, skin may be injured when the device is stripped. The poultice or gel layer may have an adhesive of Ball Nos. 3 to 9, Ball Nos. 5 to 9, Ball Nos. 7 to 9, or Ball No. 8 or 9 according to JIS Z 0237 (2000) [Test Method for Adhesive Tape and Adhesive Sheet], namely, a Ball Tack Method Using Slope, at the angle of the slope of 30 degrees.

Before use, the surface of the poultice or gel layer is covered with a releasing sheet. Namely, before use one of the outermost layers of the device is a releasing sheet layer. The materials of the releasing sheet layer are not limited as long as they have been conventionally used for a sheet to cover a layer of, e.g., a poultice composition. For example, various plastic films and composites of a plastic film and paper can be used as the releasing sheet layer. On the releasing sheet layer, a release coating agent of a silicone, alkyl acrylate, or fluorine type may be coated.

The total thickness of the gas-impermeable sheet layer that constitutes one side of the pouch and the support (if an adhesive layer exist, its thickness is also added) affects the conduction of heat that the exothermic composition generates to the poultice or gel layer. From the view point of heat conductivity, the total thickness of the gas-impermeable sheet layer and the support may be 100 to 500 µm, 100 to 400 µm, or 150 to 300 µm.

The device of the present invention is stored in a bag. The bag is made of a moisture-resistant gas-impermeable material. Because the bag is made of a gas-impermeable material, the exothermic agent contained in the exothermic composition does not cause a chemical reaction, thus the device can be stored without the generation of heat. After the bag is opened, air (especially, oxygen) gets in from the gas-permeable side of the pouch and reaches to the exothermic agent. Thus, a chemical reaction starts and the heat is generated.

An example of the material for the bag is a laminate of an aluminium thin layer and a polymer film.

The present invention also relates to an adhesive structure comprising a support, an adhesive poultice or gel layer, and a releasing sheet layer in this order, wherein the support comprises a fibrous layer only or a gas-impermeable sheet and a fibrous layer and has a moisture permeability within the range of 0 to 3,000 g/m$^2$·24 hours by the Lyssy method (JIS K 7129). This structure has a form of sheet, commonly a long sheet, and can be used to prepare the device of the present invention. The parts that are expressed by the numeral 30 in FIGS. 1 and 2 are derived from this structure.

The details of the elements or components of this structure are the same as those that have been explained about the device of the present invention.

This structure is made by, e.g., applying or coating a composition that is used to prepare a poultice or gel layer on a fibrous layer of a support by using a coater of a added gravure printing system, a screen printing system, or the like to prepare the poultice or gel layer. At about the same time of the preparation of the poultice or gel layer, the surface of the poultice or gel layer is covered with a releasing sheet. Or, first, a composition that is used to prepare a poultice or gel layer is cast on a film. Next, a polymer contained in the composition is crosslinked. Thus, the composition turns into a membrane. Then, the membrane is transferred onto a fibrous layer and then the surface of the poultice or gel layer is covered with a releasing sheet.

One example of the method for preparing the device of the present invention is as follows:

First, a gas-permeable sheet and a sheet composite comprising a gas-impermeable sheet layer, an adhesive layer, and a releasing paper are prepared. The gas-permeable sheet and the sheet composite are arranged so that the gas-permeable sheet faces the gas-impermeable sheet layer If a self-heating and adhesive device 100 or 200 shown in FIG. 1 or 2 is to be prepared, in which an unwoven fabric layer 15 is made on a gas-permeable sheet layer 3, instead of the gas-permeable sheet, a sheet composite comprising the gas-permeable sheet layer 3 and the unwoven fabric layer 15 is used. These two sheet composites are arranged so that the gas-permeable sheet layer faces the gas-impermeable sheet layer.

The gas-permeable sheet and the sheet composite or the two sheet composites (hereafter, "sheet composites") are heat-sealed in their lateral direction, and then both sides are heat-sealed in their longitudinal directions. Thus, a room is made. An exothermic composition is stuffed in this room. Again, the sheet composites are heat-sealed in their lateral direction and then in both sides in their longitudinal directions to make a room. Again, an exothermic composition is stuffed in this room. The room in which the exothermic composition is stuffed is pressed. Thus, the exothermic composition turns into a layer. A series of the operations are repeated. Thus, rooms in which the exothermic composition is stuffed are obtained in a continuous form.

Aside from this, the structure of the present invention, namely, an adhesive structure comprising a support, an adhesive poultice or gel layer, and a releasing sheet layer in this order is prepared. This structure has also a sheet form.

The releasing paper is peeled off, and to the adhesive layer thus exposed the adhesive structure of the present invention is bonded. To the adhesive layer the fibrous layer as the support in the adhesive structure is bonded, if the support comprises the fibrous layer only. To the adhesive layer the gas-impermeable sheet of the support in the adhesive structure is bonded, if the support comprises the fibrous layer and the gas-impermeable sheet. Thus, the devices of the present invention are obtained in a continuous form.

Next, one device is cut off by making a cut at the lateral heat-sealed portion. At once, the device is put into a bag that is made of an oxygen-impermeable material and the opening of the bag is closed. These operations are repeated.

Just before the device of the present invention is used, the device is get out from the bag, the releasing sheet layer is peeled off, and the device is applied on a part of a human body.

EXAMPLES

Hereafter, examples of the present invention will be explained. However, the scope of the present invention is not limited by these examples.

Example 1

An exothermic composition was prepared according to the formula shown in Table 1. A composition that would be used to prepare a poultice layer was also prepared according to the formula shown in Table 2.

TABLE 1

| Raw materials | Amounts (wt. %) |
|---|---|
| Iron powder | 60 |
| Active carbon | 5 |
| Carboxymethyl cellulose | 2 |
| Acrylic acid starch | 2 |
| Sodium chloride | 2 |
| Water | 29 |
| Total | 100 |

TABLE 2

| Raw materials | Amounts (wt. %) |
|---|---|
| Poly(vinyl alcohol) | 3.000 |
| Acrylic acid starch | 1.000 |
| Carboxymethyl cellulose | 1.000 |
| Kaolin | 11.000 |
| Titanium oxide | 1.000 |
| Sorbitan monolaurate | 0.050 |
| Tartaric acid | 0.300 |
| Poly(acrylic acid) | 8.000 |
| Liquid paraffin | 1.000 |
| Sorbitol | 3.000 |
| Sorbitan (polyoxyethylene) monopalmitate | 0.050 |
| Butyl para-hydroxybenzoate | 0.050 |
| Methyl para-hydroxybenzoate | 0.050 |
| Propylene glycol | 0.050 |
| Poly(sodium acrylate) | 5.000 |
| Dried alminium hydroxide gel | 0.060 |
| Magnesium metasilicate aluminate | 0.015 |
| Sodium edetate (EDTA-Na) | 0.015 |
| Conc. Glycerol | 12.000 |
| Water | balance |
| Total | 100.000 |

A sheet composite (I) was used in which a layer of an adhesive, of which main component was SIS (styrene-isoprene-styrene block copolymer), was made on a commercially available, gas-impermeable polyethylene film (thickness: 40 μm) and in which the surface of the layer of the adhesive was covered by a releasing paper. Also, a sheet composite A comprising a gas-permeable porous polyethylene film (manufactured by Kojin; thickness: 50 μm) and a polyester (100%) spun-lace unwoven fabric (manufactured by Asahikasei; basis weight: 90 g/m$^2$) was used. The sheet composite A has a moisture-permeability of 250 g/m$^2$·24 hours by the Lyssy method (JIS K 7129).

The machine that was used to determine the moisture-permeability was type L80-4000, manufactured by Lyssy. The temperature was 40° C., and the relative humidity was 90%.

The sheet composite (I) was lapped over the sheet composite A so that the gas-impermeable polyethylene film of the sheet composite (I) faced the gas-permeable porous polyethylene film of the sheet composite A and they were heat-sealed in their lateral direction. Next, both sides were heat-sealed in their longitudinal direction. Thus, a room was made. The exothermic composition (20 g) that had been prepared according to the formula of Table 1 was stuffed in this room. Again, the sheet composite (I) and the sheet composite A were heat-sealed in their lateral direction and then in both sides in their longitudinal directions to make a room. Again, the same exothermic composition (20 g) was stuffed in this room. The room in which the exothermic composition had been stuffed was pressed. Thus, the exothermic composition turned into a layer having a thickness of about 1.5 mm. A series of the operations were repeated. Thus, an exothermic structure having continuous rooms in which the exothermic composition was stuffed was obtained.

Aside from this, an adhesive structure a was prepared. A polypropylene (100%) melt-blow unwoven fabric (manufactured by Kurare; basis weight: 40 g/m$^2$) having a moisture-permeability of 1,890 g/m$^2$·24 hours by the Lyssy method (JIS K 7129) was used. On this unwoven fabric, the composition having the formula of Table 2 was applied in an amount of 500 g/m$^2$ to prepare a layer and then the surface of the layer was covered with a releasing sheet.

The releasing paper of the exothermic structure was peeled off, and to the adhesive layer thus exposed the unwoven fabric of the adhesive structure a was bonded. Thus, continuous self-heating and adhesive poultice devices were obtained.

Next, by making a cut at the lateral heat-sealed portion, one device as shown in FIG. 1 was cut off. At once, the device was put into a bag that was made of an oxygen-impermeable material and the opening of the bag was dosed.

The thickness of one side of the self-heating and adhesive poultice devices, i.e., the total thickness of the gas-impermeable polyethylene film, the adhesive (SIS) layer, and the polypropylene melt-blow unwoven fabric, was 270 μm.

The self-heating and adhesive poultice devices (100 pieces) were examined about the adhesive bonding between the gas-impermeable polyethylene film and the polypropylene melt-blow unwoven fabric. None was insufficiently bonded.

Example 2

A sheet composite (II) was used in which a layer of an adhesive, of which main component was SIS (styrene-isoprene-styrene block copolymer), was made on a commercially available, gas-impermeable polyethylene film (thickness: 25 μm) and in which the surface of the layer of the adhesive was covered by a releasing paper. Also, a sheet composite A comprising a gas-permeable porous polyethylene film (manufactured by Kojin; thickness: 50 μm) and a polyester (100%) spun-lace unwoven fabric (manufactured by Asahikasei; basis weight: 90 g/m$^2$) was used. The sheet composite A has a moisture-permeability of 250 g/m$^2$·24 hours by the Lyssy method (JIS K 7129).

The sheet composite (II) was lapped over the sheet composite A so that the gas-impermeable polyethylene film of the sheet composite (II) faced the gas-permeable porous polyethylene film of the sheet composite A and they were heat-sealed in their lateral direction. Next, both sides were heat-sealed in their longitudinal directions. Thus, a room was made. The exothermic composition (20 g) that had been prepared according to the formula of Table 1 was stuffed in this room. Again, the sheet composite (II) and the sheet composite A were heat-sealed in their lateral direction and then in both sides in their longitudinal directions to make a room. Again, the same exothermic composition (20 g) was stuffed in this room. The room in which the exothermic composition had been stuffed was pressed. Thus, the exothermic composition turned into a layer having a thickness of about 1.5 mm. A series of the operations were repeated. Thus, an exothermic structure having continuous rooms in which the exothermic composition was stuffed was obtained.

Aside from this, an adhesive structure b was prepared.

To prepare the adhesive structure b, a sheet composite B was used in which by using a layer of an adhesive, of which main component was SIS (styrene-isoprene-styrene block copolymer), a commercially available, gas-impermeable polyethylene film (thickness: 25 μm) and a polyester (100%) spun-lace unwoven fabric (manufactured by Asahikasei; basis weight: 20 g/m$^2$) was bonded. The sheet composite B has a moisture-permeability of about 0 g/m$^2$·24 hours by the Lyssy method (JIS K 7129).

On the unwoven fabric of the sheet composite B, the composition having the formula of Table 2 was applied in an amount of 500 g/m$^2$ to prepare a layer and then the surface of the layer was covered with a releasing sheet. Thus, the adhesive structure b was prepared.

The releasing paper of the exothermic structure was peeled off, and to the adhesive layer thus exposed the gas-impermeable polyethylene film of the adhesive structure b was bonded. Thus, continuous self-heating and adhesive poultice devices were obtained.

Next, by making a cut at the lateral heat-sealed portion, one device as shown in FIG. 2 was cut off. At once, the device was put into a bag that was made of an oxygen-impermeable material and the opening of the bag was closed.

The thickness of one side of the self-heating and adhesive poultice devices, i.e., the total thickness of the gas-impermeable polyethylene film, the adhesive (SIS) layer, the gas-impermeable polyethylene film, the adhesive (SIS) layer, and the polyester spun-lace unwoven fabric (basis weight: 20 g/m$^2$), was 175 μm.

The self-heating and adhesive poultice devices (100 pieces) were examined about the adhesive bonding between two sheets of the gas-impermeable polyethylene films. None was insufficiently bonded.

Comparative Example 1

The exothermic structure having continuous rooms in which the exothermic composition was stuffed was made by the same way as that shown in Example 1.

Aside from this, an adhesive structure c was prepared. A rayon/polyester (60%/40%) spun-lace unwoven fabric (manufactured by Asahikasei; basis weight: 40 g/m$^2$) having a moisture-permeability of 3,900 g/m$^2$·24 hours by the Lyssy method (JIS K 7129) was used. On this unwoven fabric, the composition having the formula of Table 2 was applied in an amount of 500 g/m$^2$ to prepare a layer and then the surface of the layer was covered with a releasing sheet.

The releasing paper of the exothermic structure was peeled off, and a trial of bond of the unwoven fabric of the adhesive structure c to the adhesive layer thus exposed was made. However, this trial did not become successful because moisture that had been contained in the poultice composition permeated and get to the other side (i.e., a side that was to be bonded) through the spun-lace unwoven fabric.

Comparative Example 2

Continuous self-heating and adhesive poultice devices were made by the same way as that shown in Example 1, except that the composition that would be used to prepare a poultice layer was prepared according to the formula shown in Table 3. The self-heating and adhesive poultice device was put into a bag that was made of an oxygen-impermeable material and the opening of the bag was closed.

TABLE 3

| Raw materials | Amounts (wt. %) |
| --- | --- |
| Poly(vinyl alcohol) | 3.000 |
| Acrylic acid starch | 1.000 |
| Carboxymethyl cellulose | 1.000 |
| Kaolin | 11.000 |
| Titanium oxide | 1.000 |
| Sorbitan monolaurate | 0.050 |
| Tartaric acid | 0.300 |
| Poly(acrylic acid) | 8.000 |
| Liquid paraffin | 1.000 |
| Sorbitol | 3.000 |
| Sorbitan (polyoxyethylene) monopalmitate | 0.050 |
| Butyl para-hydroxybenzoate | 0.050 |
| Methyl para-hydroxybenzoate | 0.050 |
| Propylene glycol | 0.050 |
| Poly(sodium acrylate) | 5.000 |
| Dried alminium hydroxide gel | 0.080 |
| Magnesium metasilicate aluminate | 0.040 |
| Sodium edetate (EDTA-Na) | 0.030 |
| Conc. Glycerol | 12.000 |
| Water | balance |
| Total | 100.000 |

Experimental Test 1

Self-heating and adhesive poultice devices were examined about their temperature-retaining properties. The machine that was used for the experimental test 1 and the examination method are shown hereafter.

Test Machine

The machine comprises a heating device and a temperature controlled tank of a water circulation system.

(1) Heating Device

The material for the heating device is SUS 304 (thickness: 3 mm) regulated in JIS G 4303 (hot rolled stainless steel). It has a form of a box and the sizes are 300 mm (length)×600 mm (width)×100 mm (height). On the upper surface of the heating device, a plate that is made of an acrylic resin and has a thickness of 6 mm is fixed with screws. Surfaces other than the upper surface is covered by a heat insulating material that is made of an expanded polystyrene and has a thickness of 30 mm Inside the heating device, warm water circulates.

(2) Temperature Controlled Tank of Water Circulation System

This is a tank through which warm water can circulate in a flow rate of 19 to 21 liter per minute.

In this examination test, the water temperature was controlled so that the temperature on the acrylic resin plate was 35 to 37° C.

Examination Method (1) The self-heating and adhesive poultice device of Example 1 or 2 was taken out of the bag.

(2) The releasing sheet was peeled off and the poultice layer was applied onto the acrylic resin plate (at a temperature of 35 to 37° C.). A thermometer was put in between the poultice layer and the acrylic resin plate.

(3) The temperature was determined at regular time intervals.

The results are shown in Table 4.

TABLE 4

| | Temperature change (° C.) | | | | | | | | | Highest temperature (° C.) |
| --- | --- | --- | --- | --- | --- | --- | --- | --- | --- | --- |
| | 0 min. | 30 min. | 1 hour | 2 hours | 3 hours | 4 hours | 5 hours | 6 hours | 7 hours | 8 hours | |
| Example 1 | 32.9 | 43.0 | 43.1 | 42.8 | 42.2 | 41.6 | 41.2 | 40.8 | 40.8 | 40.9 | 43.1 |
| Example 2 | 32.8 | 42.3 | 42.3 | 42.0 | 41.3 | 40.8 | 40.3 | 39.9 | 40.0 | 40.1 | 42.3 |

As is clear from the results shown in Table 4, the self-heating and adhesive poultice devices of the present invention show good heat conductivity. Thus, the temperature of the poultice layer, where contacts a human body, was maintained within an appropriated range for a long period of time, i.e., over eight hours.

Experimental Test 2

The self-heating and adhesive poultice devices of Examples 1 and 2, and Comparative Example 2 were used.

The device that was enclosed in the bag was stored at room temperatures. After three days, the device was taken out of the bag. The releasing sheet was peeled off and then the adhesive force of the poultice layer was determined according to JIS Z 0237 (2000), i.e., the Test Method for Adhesive Tape and Adhesive Sheet (angle of the slope: 30 degrees; balls used: Nos. 1-9).

The reason why the devices were stored for three days at room temperatures is to stabilize the condition of closslinking of the water-soluble polymers.

The same operations were repeated, except that self-heating and adhesive poultice devices that were stored at room temperatures for forty five days and those that were stored at 40° C. for fifteen days were used.

The results are shown in Table 5.

TABLE 5

| | 3 days after preparation (stored at room temperatures) | 45 days after preparation (stored at room temperatures) | 15 days after preparation (stored at 40° C.) |
| --- | --- | --- | --- |
| Example 1 | 9+* | 9+* | 9+* |
| Example 2 | 9+* | 9+* | 9+* |
| Comparative Example 2 | 9+* | 5 | 6 |

*The ball did not move even after five seconds, which is a period of time that is regulated in JIS 0237 (2000).

As is clear from the results shown in Table 5, the adhesive forces of the self-heating and adhesive poultice devices of the present invention are not reduced due to their storage. In contrast, the adhesive forces of the conventional self-heating and adhesive poultice device, i.e., Comparative Example 2 (in which the amount of the closslinking agent is increased to prevent the permeation of the composition for the poultice layer to the other side of the unwoven fabric), is reduced with the lapse of time.

The present invention is defined or limited only by the following claims.

What we claim are:

1. A process for preparing a self-heating and adhesive device comprising:
   1) providing a gas-permeable sheet layer or a composite of a gas-permeable sheet layer and an unwoven fabric layer;
   2) providing a sheet composite comprising a gas-impermeable sheet layer, an adhesive layer, and a releasing paper in this order;
   3) bonding or heat-sealing the gas-permeable sheet layer and the gas-impermeable sheet layer to make a pouch having an opening;
   4) stuffing an exothermic composition into the pouch;
   5) closing the opening of the pouch by bonding or heat-sealing;
   6) preparing a composite of a support and a poultice or gel layer whose surface is covered with a releasing sheet, wherein the support comprises a fibrous layer only or a gas-impermeable sheet and a fibrous layer and has a moisture permeability within the range of 0 to 3,000 g/m$^2$·24 hours by the Lyssy method and wherein the poultice or gel layer is made on the fibrous layer;
   7) peeling off the releasing paper;
   8) bonding an outer surface of the support to the adhesive layer; and
   9) cutting off one self-heating and adhesive device.

2. The process according to claim 1, wherein the support comprises a gas-impermeable sheet and a fibrous layer.

3. The process according to claim 1, wherein the poultice or gel layer has an adhesive force of Ball Nos. 7 to 9 according to a Ball Tack Method using a slope at an angle of 30 degrees [JIS Z 0237 (2000)].

4. The process according to claim 3, wherein the poultice or gel layer is made by using a composition comprising a polymer; an excipient, filler, or vehicle; a cross-linking agent; a polyhydric alcohol; a surfactant; a preservative or stabilizer; and water.

5. The process according to claim 4, wherein the composition comprises water in an amount of about 50 to 60% by weight.

6. The process according to claim 3, wherein the poultice or gel layer has an adhesive force of Ball Nos. 7 to 9 after 45 days from the preparation of the adhesive structure.

7. The process according to claim 1, wherein the poultice or gel layer is made by using a composition comprising a polymer; an excipient, filler, or vehicle; a cross-linking agent; a polyhydric alcohol; a surfactant; a preservative or stabilizer; and water.

8. The process according to claim 7, wherein the composition comprises water in an amount of about 50 to 60% by weight.

* * * * *

UNITED STATES PATENT AND TRADEMARK OFFICE
CERTIFICATE OF CORRECTION

PATENT NO. : 7,621,110 B2
APPLICATION NO. : 11/405147
DATED : November 24, 2009
INVENTOR(S) : Ota et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 849 days.

Signed and Sealed this

Twenty-sixth Day of October, 2010

David J. Kappos
*Director of the United States Patent and Trademark Office*